(12) United States Patent
Kim

(10) Patent No.: US 7,435,219 B2
(45) Date of Patent: Oct. 14, 2008

(54) SURGICAL RETRACTOR POSITIONING DEVICE

(75) Inventor: Daniel H. Kim, Mountain View, CA (US)

(73) Assignee: DePuy Spine, Inc., Raynham, MA (US)

( * ) Notice: Subject to any disclaimer, the term of this patent is extended or adjusted under 35 U.S.C. 154(b) by 625 days.

(21) Appl. No.: 10/808,687

(22) Filed: Mar. 25, 2004

(65) Prior Publication Data

US 2005/0215866 A1  Sep. 29, 2005

(51) Int. Cl.
A61B 1/32 (2006.01)
A61B 17/02 (2006.01)

(52) U.S. Cl. .................. 600/233; 600/234

(58) Field of Classification Search .......... 600/232, 600/231, 233, 234, 201, 210, 213, 227
See application file for complete search history.

(56) References Cited

U.S. PATENT DOCUMENTS

| | | | | |
|---|---|---|---|---|
| 1,839,726 A | * | 1/1932 | Arnold ................. 600/233 |
| 3,522,799 A | | 8/1970 | Gauthier |
| 3,998,217 A | * | 12/1976 | Trumbull et al. ........ 600/233 |
| 4,010,741 A | * | 3/1977 | Gauthier ............... 600/234 |
| 4,254,763 A | * | 3/1981 | McCready et al. ....... 600/230 |
| 4,355,631 A | | 10/1982 | LeVahn |
| 4,747,394 A | | 5/1988 | Watanabe |
| 5,020,933 A | * | 6/1991 | Salvestro et al. ......... 403/90 |
| 5,052,373 A | | 10/1991 | Michelson |
| 5,125,396 A | * | 6/1992 | Ray ..................... 600/208 |
| 5,284,129 A | | 2/1994 | Agbodoe et al. |
| 5,363,841 A | | 11/1994 | Coker |
| 5,512,038 A | | 4/1996 | O'Neal et al. |
| 5,520,610 A | | 5/1996 | Giglio et al. |
| 5,688,223 A | | 11/1997 | Rosendahl |
| 5,902,233 A | | 5/1999 | Farley et al. |
| 5,928,139 A | | 7/1999 | Koros et al. |
| 5,944,658 A | | 8/1999 | Koros et al. |
| 5,984,867 A | * | 11/1999 | Deckman et al. ......... 600/232 |
| 6,007,487 A | | 12/1999 | Foley et al. |
| 6,139,493 A | | 10/2000 | Koros et al. |
| 6,187,000 B1 | | 2/2001 | Davison et al. |
| 6,214,004 B1 | | 4/2001 | Coker |
| 6,500,116 B1 | | 12/2002 | Knapp |
| 2003/0191371 A1 | | 10/2003 | Smith et al. |
| 2004/0002629 A1 | | 1/2004 | Branch et al. |

FOREIGN PATENT DOCUMENTS

FR  2 807 313 A1  10/2001

* cited by examiner

Primary Examiner—Pedro Philogene
(74) Attorney, Agent, or Firm—Nutter, McClennen & Fish LLP

(57) ABSTRACT

A surgical retractor positioning device is provided to create a surgical working field in a minimally invasive and flexible manner. In one embodiment, the device can include a frame and an arm connected to the frame. The arm can include a proximal end, a distal end having a distal end axis, and a major axis, wherein the distal end axis is movable relative to the proximal end, whereby the distal end axis can intersect the major axis at an angle. The device can include at least one blade connected to the distal end of the arm, wherein the blade is fixably rotatable about the major axis. The device can include at least two arms.

30 Claims, 16 Drawing Sheets

SURGICAL RETRACTOR POSITIONING DEVICE

BACKGROUND OF THE INVENTION

In surgical procedures, it is important to minimize trauma to the patient and damage to the tissue as much as possible. For that reason, surgeons try to keep incisions to a minimum while performing surgical procedures. However, the surgeon performing a delicate surgery must still be able to have a clear view of the operating field. Surgeons utilize retractors in an attempt to achieve the goal of keeping the incision to a minimum while still providing a clear view of the operating field.

However, many current retractors have several shortcomings. For instance, it is often difficult to minimize the size of an incision and potential trauma while expanding or changing an operating field because current retractor systems typically provide a limited amount of maneuverability of the retractor blades. For example, some current retractor systems merely include retractor blades that are only able to translate along a limited number of axes. Expansion of the operating field with such a retractor system requires an increase of the incision size due to the translation of the retractor blades.

Therefore, there is a need to develop a new retractor system that provides the surgeon with a greater flexibility to explore and create an operating field and perform surgical procedures in a minimally invasive manner.

SUMMARY OF THE INVENTION

The present invention provides a surgical retractor that includes a retractor positioning device to create a surgical working field in a minimally invasive and flexible manner. In one embodiment, the device can include a frame and an arm connected to the frame. The arm can include a proximal end, a distal end having a distal end axis, and a major axis, wherein the distal end axis is movable relative to the proximal end, whereby the distal end axis can intersect the major axis at an angle. The device can include at least one blade connected to the distal end of the arm, wherein the blade is fixably rotatable about the major axis. This allows the surgeon greater flexibility in working with the operating field.

In particular embodiments, the device can include at least two arms, wherein at least one arm is movable relative to the frame. A blade can be connected to the distal end of the second arm. An assembly device can be provided that includes a collar or rack to facilitate positioning the blades onto the arms. Each blade includes a proximal end, a distal end, and a major axis that extends between the proximal and distal ends. The major axes of the blades can be supported substantially in parallel when suspended from the rack at the proximal end. In other embodiments, the major axes of the blades can be tapered when suspended from the rack.

In other embodiments, the major axes of the arms are colinear or intersect. The device can include at least four arms, each of which having a major axis that is colinear or intersects the major axis of each of the other arms. At least one arm can be movable along its major axis. In another embodiment, the major axis of at least one arm can pivot about a point at the frame. At least one portion of the frame along which the arm is movable can be arcuate. In specific embodiments, the frame can be substantially circular or substantially elliptical.

The blade can include a clip for removably connecting the blade to the arm. The blade can be at least partially tapered from an end, which is attachable to the arm, to a working end. In other embodiments, the blade can include an outer surface that is configured to prevent or minimize soft tissue slip during retraction. The blade can be detachable from the arm.

In other embodiments, a sensor can be provided at at least one blade. The sensor can be at least one member selected from the group consisting of a pressure sensor, a thermal sensor, and a motion sensor. In other embodiments, at least one blade can include a position sensor. The position sensor can be at least one member selected from the group consisting of a reflective, a light-emitting, and an RF-emitting sensor.

In other embodiments, the arm can be controlled by a controller coupled to an actuator. The device can include one or more sensors at the arm, blade, or a combination thereof, coupled to the controller, whereby the controller controls the arm based on information provided by the sensor(s).

In other embodiments, a surgical retractor positioning device is provided which includes a circular frame and a plurality of arms connected to the frame. Each arm can include a proximal end, a distal end having a distal end axis being movable relative to the proximal end, and a major axis that extends between the proximal and distal ends, whereby the distal end axis can intersect the major axis at an angle. The device can further include a retractor blade connected to the distal end of each arm, wherein each blade is fixably rotatable about the major axis.

Each blade can include a clip for removably connecting the blade to an arm. A retractor blade assembly can be provided for attaching the blades to the distal end of each arm.

A method of forming a surgical working field in a patient is further provided, which can include the steps of making an incision in a patient and positioning a surgical retractor over the incision. The retractor can include a plurality of blades connected to respective arms positioned on a frame. Each arm can include a major axis, a proximal end, and a distal end having a distal end axis. Each blade can be connected to the distal end, wherein the distal end axis is movable relative to the proximal end, whereby the distal end axis can intersect the major axis at an angle. The blades can be adjustable from a collapsed, reduced diameter configuration to an extended, increased diameter configuration.

The method can further include the steps of introducing the blades in the collapsed configuration into the incision in the patient, expanding the blades within the incision to the increased configuration to create the working field in the patient, and rotating at least one blade relative to a major axis of an arm and affixing the blade in a desired position. The steps of moving the at least one retractor blade can be carried out under automated control. The method can further include the step of connecting the plurality of blades to the respective arms with a rack.

A retractor blade assembly can be provided in accordance with other embodiments. In one embodiment, the retractor blade assembly can include a rack and at least two retractor blades. Each retractor blade can include a proximal end, a distal end, and a major axis that extends between the proximal and distal ends. The major axes of the retractor blades can be supported substantially in parallel, or tapered, when suspended from the rack at the proximal end.

Hooks can be provided at the rack for coupling the retractor blades thereto. The retractor blades can include at least one clip at the proximal end, whereby each retractor blade can be affixed to the distal end of an arm of a surgical retractor. Each hook at the rack can be slidably engageable with the at least one clip of the retractor blade while the blades are suspended within the rack.

A method of forming a surgical working field in a patient is further provided, comprising the steps of making an incision in a patient, introducing a plurality of retractor blades into the incision in the patient, attaching the blades to a plurality of arms of a surgical retractor, and removing a rack attached to the blades. The method can further include positioning the surgical retractor over the incision in the patient. The retractor can include the plurality of arms attached to a frame, with each arm being positioned to receive a retractor blade.

The method can also include attaching the plurality of blades to the rack after the surgical retractor is positioned over the incision and expanding the frame, thereby retracting the incision with the blades to form the surgical working field in the patient.

The invention has many advantages. For example, the invention provides for increased flexibility in manipulating the operating field in the patient. A mechanism is provided to quickly attach a plurality of retractor blades to the frame.

DETAILED DESCRIPTION OF THE INVENTION

Figure 1:
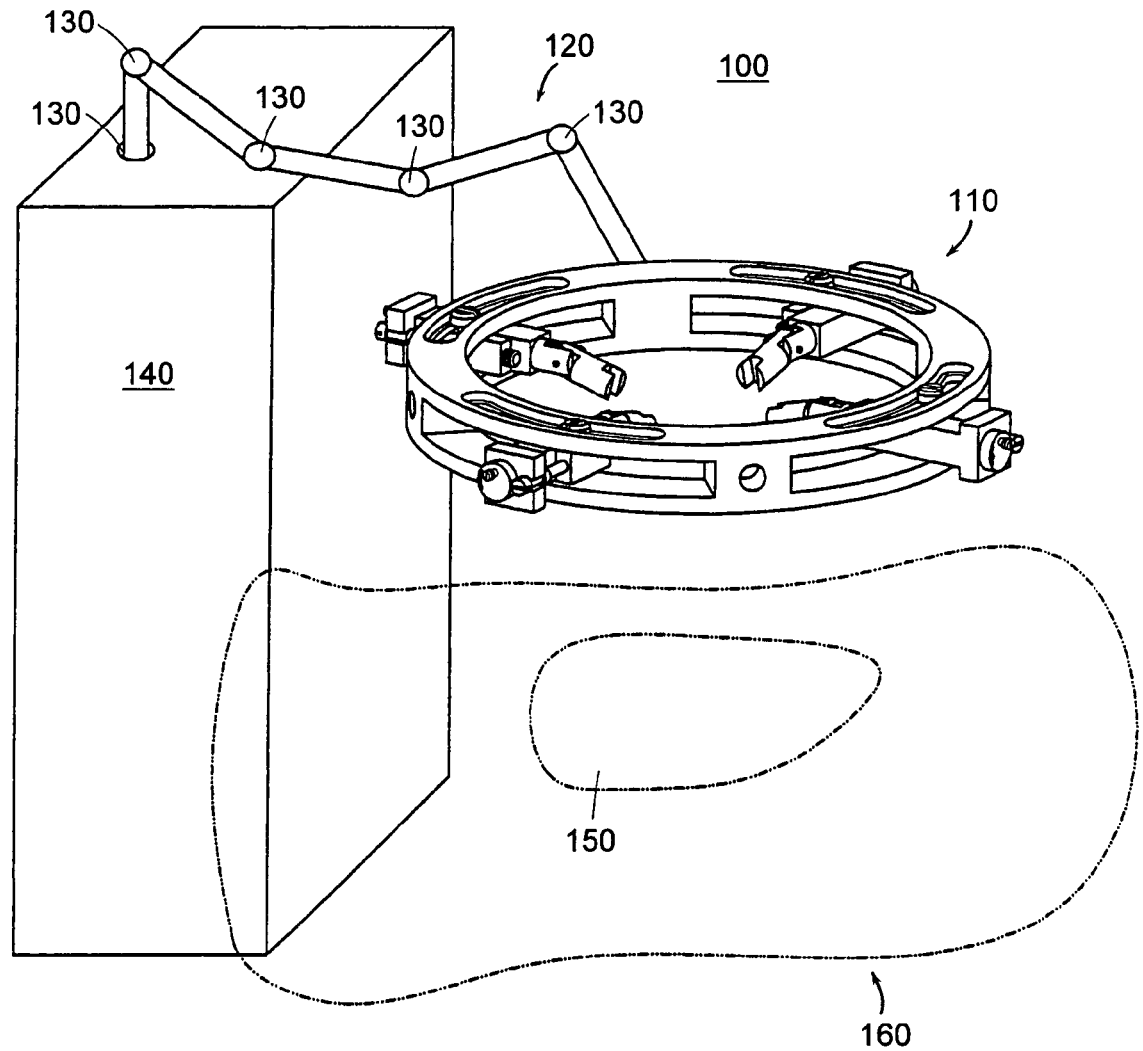
FIG. 1 is a perspective view of an embodiment of a surgical retractor positioned over an incision by a surgical arm.

The foregoing and other objects, features and advantages of the invention will be apparent from the following more particular description of various embodiments of the invention, as illustrated in the accompanying drawings in which like reference characters refer to the same parts throughout the different views. The drawings are not necessarily to scale, emphasis instead being placed upon illustrating the principles of the invention.

The present invention includes one embodiment of an adjustable retractor 100 of the invention for minimally invasive surgical access. The retractor 100 includes a frame 110 that is attachable to an arm 120 as shown in FIG. 1. Arm 120 is attached to a supporting structure 140, which can, for example, be a table, a rack, a cart, or the like. Arm 120 is preferably a surgical arm, such as a universal arm, which includes enough joints 130 to provide a desired number of degrees of freedom to easily adjust frame 110 over an incision 150 in a patient 160 (illustratively shown by a drape over the patient). Utilizing and moving arm 120 allows frame 110 to be positioned in a substantially stationary position over the surgical access site. Frame 110 can provide a working support for the surgeon to rest his/her hands or arms on while performing a surgical procedure. Joints 130 can include either a mechanism or a certain stiffness that allows the surgeon to position the surgical arm easily to a desired position and maintain the surgical arm 120 in the new position.

Figure 2:
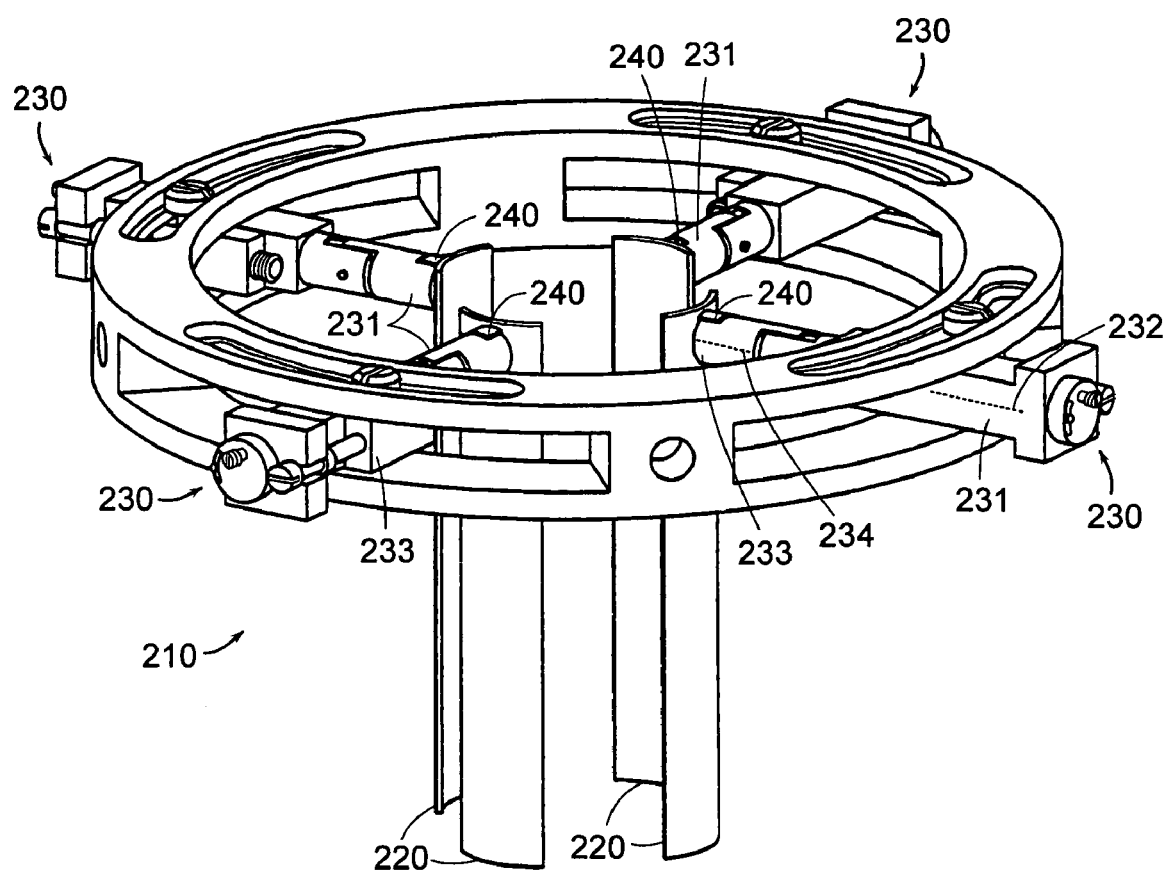
FIG. 2 is a perspective view of the frame shown in FIG. 1 having surgical retractor blades movably attached thereto.

FIG. 2 shows frame 210 with surgical retractor blades 220 that can be movably attached to frame 210. Surgical retractor blades 220 are preferably attached to the inside of frame 210 in a particular embodiment. Once frame 210 is positioned over an incision, preferably a small minimally invasive incision, each surgical retractor blade 220 can be inserted into a body cavity through the incision. The surgical retractor blade(s) 220 can also create a body cavity through insertion or retraction.

Once the surgical retractor blade 220 is inserted inside the body, the surgical retractor blade can be movably attached to positioning means 230. An arm or positioning means 230 provides the means to change the position of a surgical retractor blade 220 and can be changed by a translation in an X, Y, and/or Z direction and/or a rotation about X, Y, and/or Z axes. In one embodiment, the retractor 100 allows independent control over the position of each surgical retractor blade 220. That is, the positioning means 230 includes a proximal end 231 and a distal end 233, to which retractor blade 220 can be attached. The distal end 233 includes a distal end axis 234, whereby the distal end of the positioning means 230 is fixably rotatable about a major axis 232 extending from proximal end 231 to the distal end 233 when the distal end axis 234 is colinear with major axis 232. The term "fixably rotatable," as defined herein means that distal end 233 is, alternatively, fixed or rotatable, about a major axis extending from proximal end 231 to distal end 233 when the distal end axis 234 is colinear with the major axis 232. Optionally, the distal end 233 is movable relative to the proximal end 231, whereby the distal end axis 234 can intersect major axis 232 at an angle. This provides flexibility in manipulating the operating field in the patient.

The positioning means 230 can include attachment means 240 that is used to attach the surgical retractor blade 220 to the frame 110. The attachment means 240 can be any type of means that enables attachment, such as a screw, pin, magnet or the like. However, in a preferred embodiment, the attachment means 240 is a clip or hook-on mechanism that makes it easy to connect and disconnect the retractor blade 220 to and from the frame, respectively. In one embodiment, the surgical retractor blade 220 can have one location for attachment. In another embodiment, the surgical retractor blade 220 can have several positions for attachment to the positioning means at different heights (see also FIG. 3). This controls the depth of the surgical retractor blade 220 in the body, which is beneficial to cover surgical procedures at various depths subcutaneously. The attachment means is secure enough to keep the surgical retractor blades 220 attached to the positioning means 230 while the surgical retractor blades undergo force or torque during retraction.

The frame 110 is shown as a circular frame in one embodiment. However, the present invention is not limited to a circular frame 110 since the frame can take any shape, such as elliptical, as long as it is able to provide a base for the retractor blades 220. In particular embodiments, the number of retractor blades 220 can be two or more. Preferably, the retractor blades 220 have a curved shape as shown in FIG. 2. The curved shape allows the blades 220 to create a cylinder, channel, cannula, or the like. The size of the retractor blades 220 is dependent on the type of surgical procedure. For delicate procedures, small or miniature blades 220 are preferred, while for macroscopic procedures, blades that are less constrained in size can be used. The retractor blades 220 can be made of material that is acceptable for surgical procedures. The blades 220 can be elongated and curved. The retractor blades 220 should maintain sufficient stiffness to maintain a retracted position, though compliant enough to avoid tissue damage. In general, any type of surgical retractor blade 220 can be used as are common in the art. Also, the type of surgical retractor blades 220 can be mixed together as well as changed or renewed during a surgical procedure.

The position of each retractor blade 220 can be changed independent from the other retractor blades, which allows a great amount of flexibility to the surgeon to explore an operating field. Furthermore, the position of each retractor blade 220 can be changed without changing the position of the frame 110, i.e., leaving the frame in the substantially stationary and fixed position over the incision. A change in operating field can be obtained by changing the position of one or more retractor blades 220.

Different kinds of gearing systems, gear notches, motors (linear and rotary), pivots, joints, as well as control mechanisms and systems can be used as part of the positioning means to establish the independent control of each retractor blade. The positioning means, for example, can be a manual positioning means or an automatic positioning means. For example, stepper motors with feedback circuitry can be controlled by a controller to provide automated control of the retractor system. The present invention is not limited to the choice of any of these options as they are available in the art and applicable to its desired use for the purposes of this invention. In one aspect, it is desirable to have a positioning means that allows for macroscopic positioning and a positioning means, added or as a separate module, for microscopic positioning or fine-tuning of the retractor blade position. Furthermore, the retractor 100 can include a control system or settings that provide certain preset or predetermined positions of the surgical retractor blade(s) 220 that can be obtained once the surgical retractor blade(s) are attached to the positioning means and placed inside the body. The various sensors, for example, the position, temperature, and pressure sensors facilitate automated control of the surgical retractor.

Figure 3:
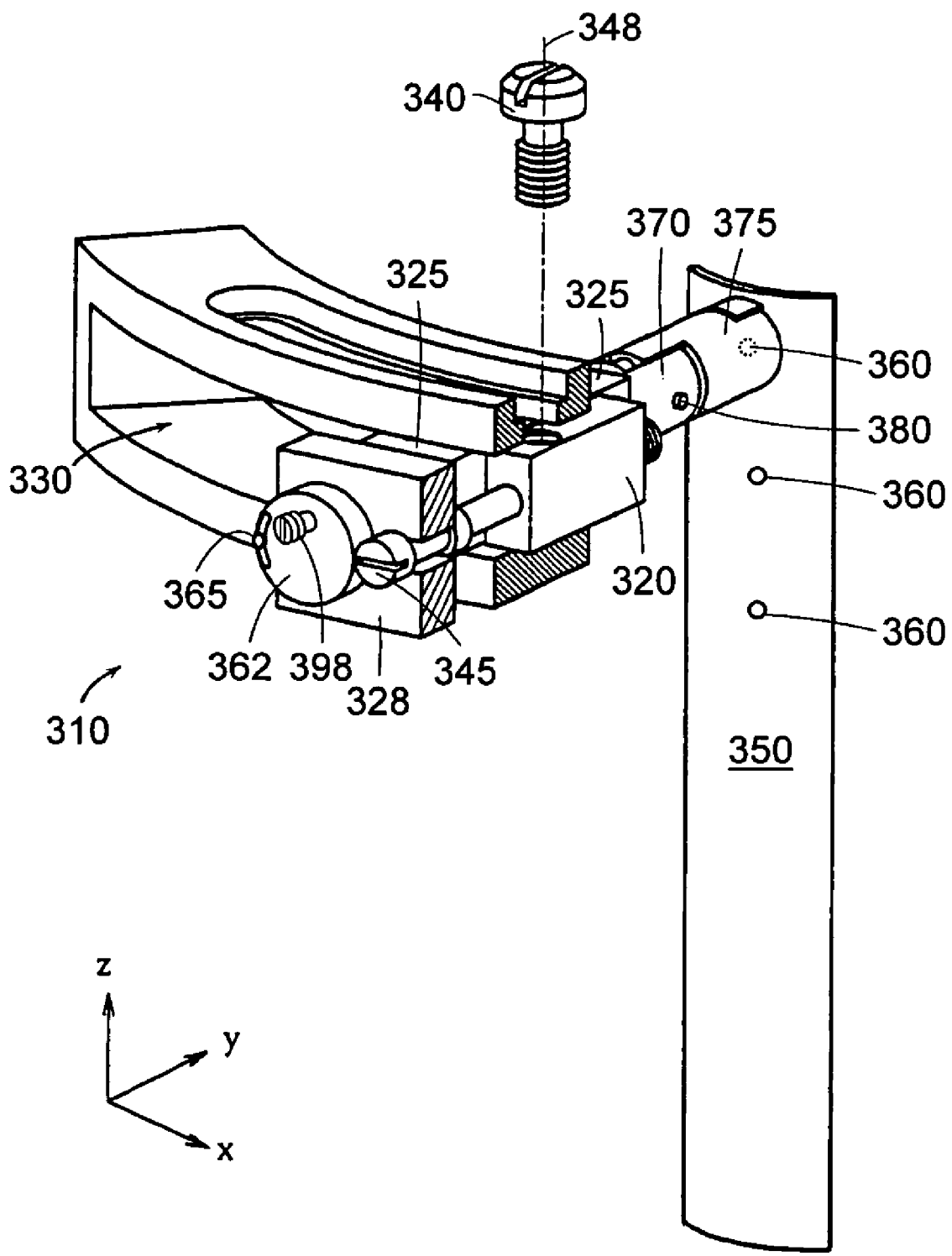
FIG. 3 is a partially cutaway perspective view of an embodiment of positioning means provided in accordance with the invention.
Figure 4:
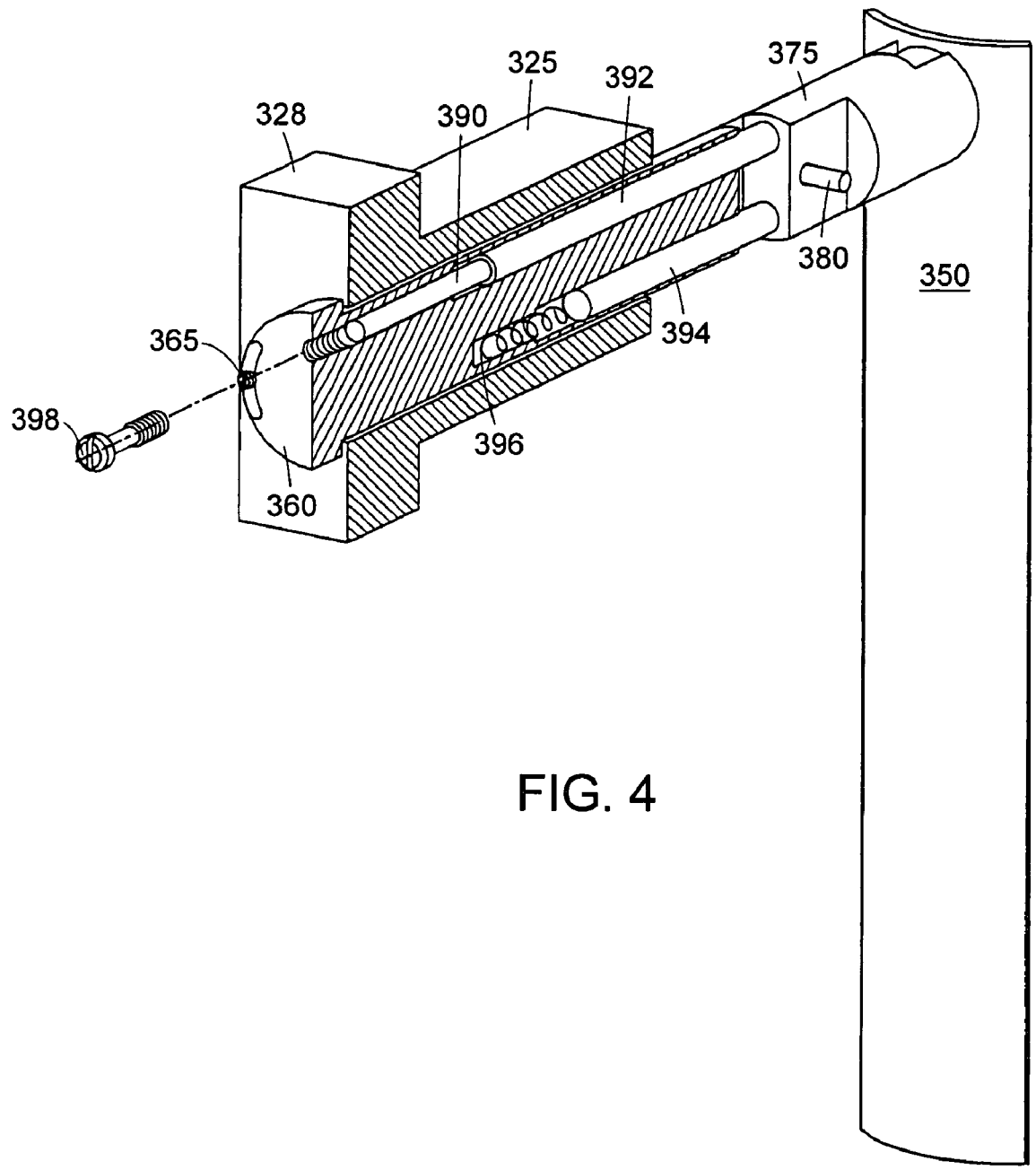
FIG. 4 is a partially cutaway perspective view of the positioning means illustrated in FIG. 3.

FIGS. 3-4 show an example of a positioning means 310 that can be used manually to position a surgical retractor blade 350 by a translation in X, Y, and/or Z directions or axes and/or a rotation about the X, Y, and/or Z axes.

It is understood that there are different ways and techniques to establish these rotations and translations, which are all included as possible positioning means for the purpose of this invention. Therefore, these examples should be regarded as illustrative rather than limiting to the scope of the present invention.

Translation in the X direction can be established by having an element 320 that is able to preferably tightly and smoothly fit and slideable in opening 330. To hold element 320 in a desired position, a fixing means 340, such as a screw, a latch, or the like, can be used. Translation in the Y direction can be established by having an element 325 that is positioned adjacent to element 320. A mechanism is further included that enables one to move element 325 in the Y direction along the side of element 320. This can be accomplished by means of a screw 345. By turning screw 345 (within element 328 that is an extended part of element 325), element 325 moves either away from or closer to element 320 therewith translating the retractor blade 350 along the Y direction. Translation in the Z direction can be established by changing the position of the surgical retractor blade 350 if more than one position 360 is available on the retractor blade.

Rotation about the Y-axis can be established by rotating a circular element 362 within element 325. Circular element 362 can have a screw-type mechanism 365 to allow the circular element 362 to be fixed at a desired position. Rotation about the Z-axis can be established by rotating element 320 around point 348. To hold element 320 in a desired position, again a fixing means 340 can be used, such as a screw, a latch, or the like.

Rotation about the X-axis can be established by pivoting elements 370, 375 about pivot point 380. Element 370 is attached to element 325 and element 375 is attached through the attachment means to surgical retractor blade 350. FIG. 4 shows an example on how such a pivoting action can be established. Circular element 362 includes a rod 390 inside a hollow tube 392. Rod 390 establishes a moment arm around pivot point 380. Another rod 394 is positioned inside circular element 362 and establishes a moment arm around pivot point 380 opposite from the moment arm that rod 390 establishes. Moving rod 390 in and out, for example, by using a screw 398, enables a rotation about the X-axis to establish toe-out or toe-in of surgical retractor blade 350.

A spring 396 enables rod 394 to push back element 375 to support toe-in when the screw is brought out (i.e., screwed out). For the toe-out motion, one needs to consider the amount of torque that would be needed to retract tissue. If a large torque is required, the moment arm can be increased with respect to the pivot point. In other embodiments, a gear system or gear notch can be provided to allow for macroscopic adjustments of a surgical retractor blade.

The examples of FIGS. 2-4 can provide independent control over all translations and rotations to establish a desired position of the surgical retractor blade. However, it is not always necessary to have all degrees of freedom available and therefore it might be desirable to freeze, constrain, or simply reduce the undesired degrees of freedom.

Figure 5:
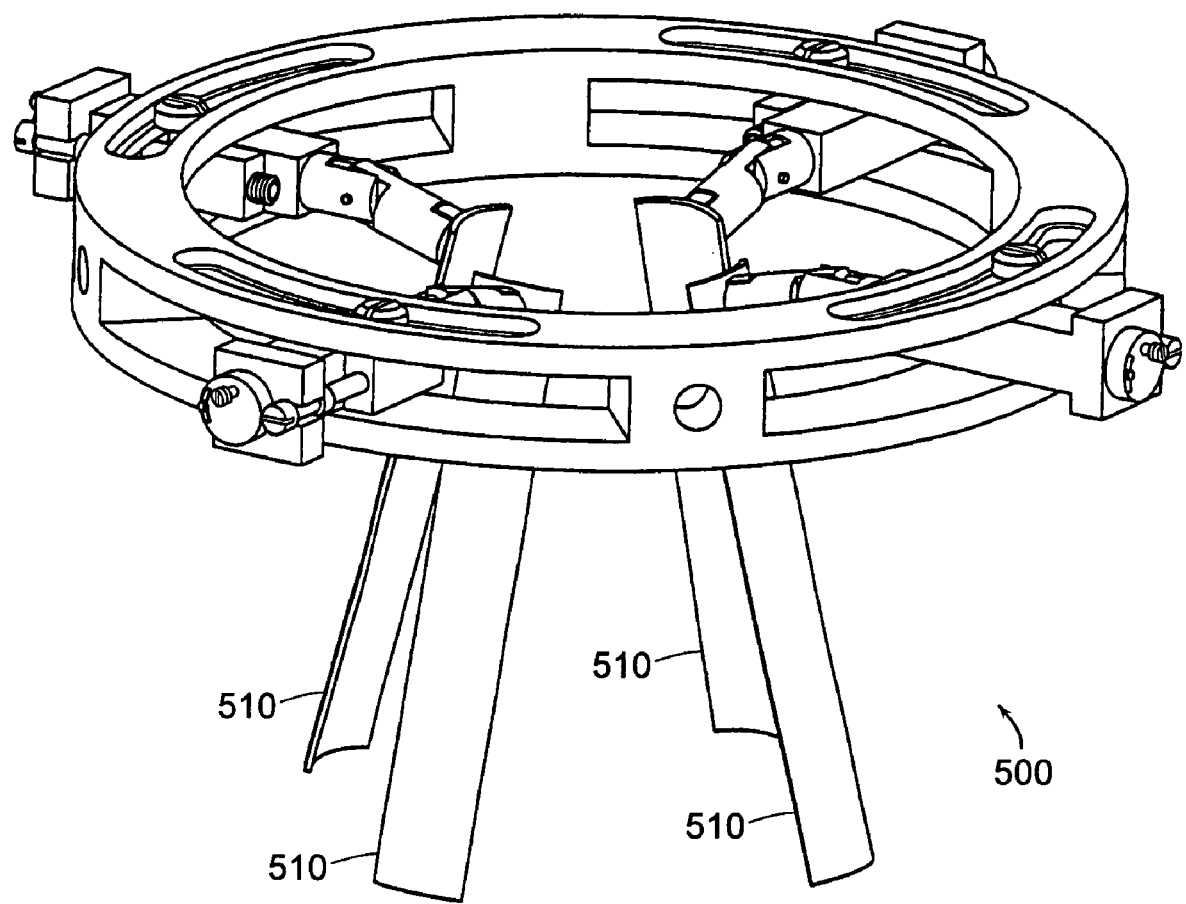
FIG. 5 is a perspective view of a surgical retractor of FIG. 1 having the retractor blades positioned in a toe-out arrangement.
Figure 6:
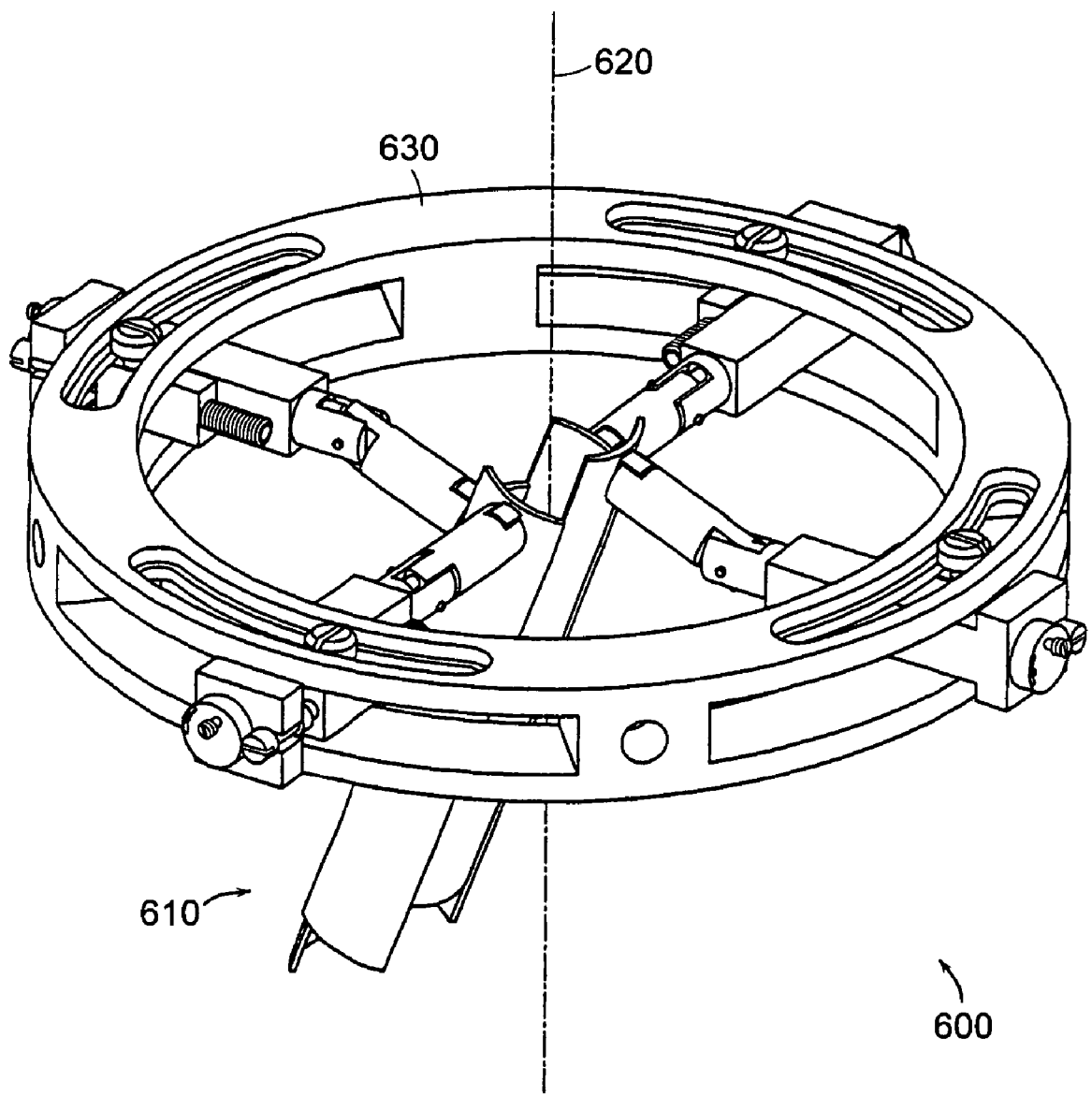
FIG. 6 is a perspective view of a surgical retractor of FIG. 1 having the retractor blades positioned to form a channel away from a central axis of the frame.
Figure 7:
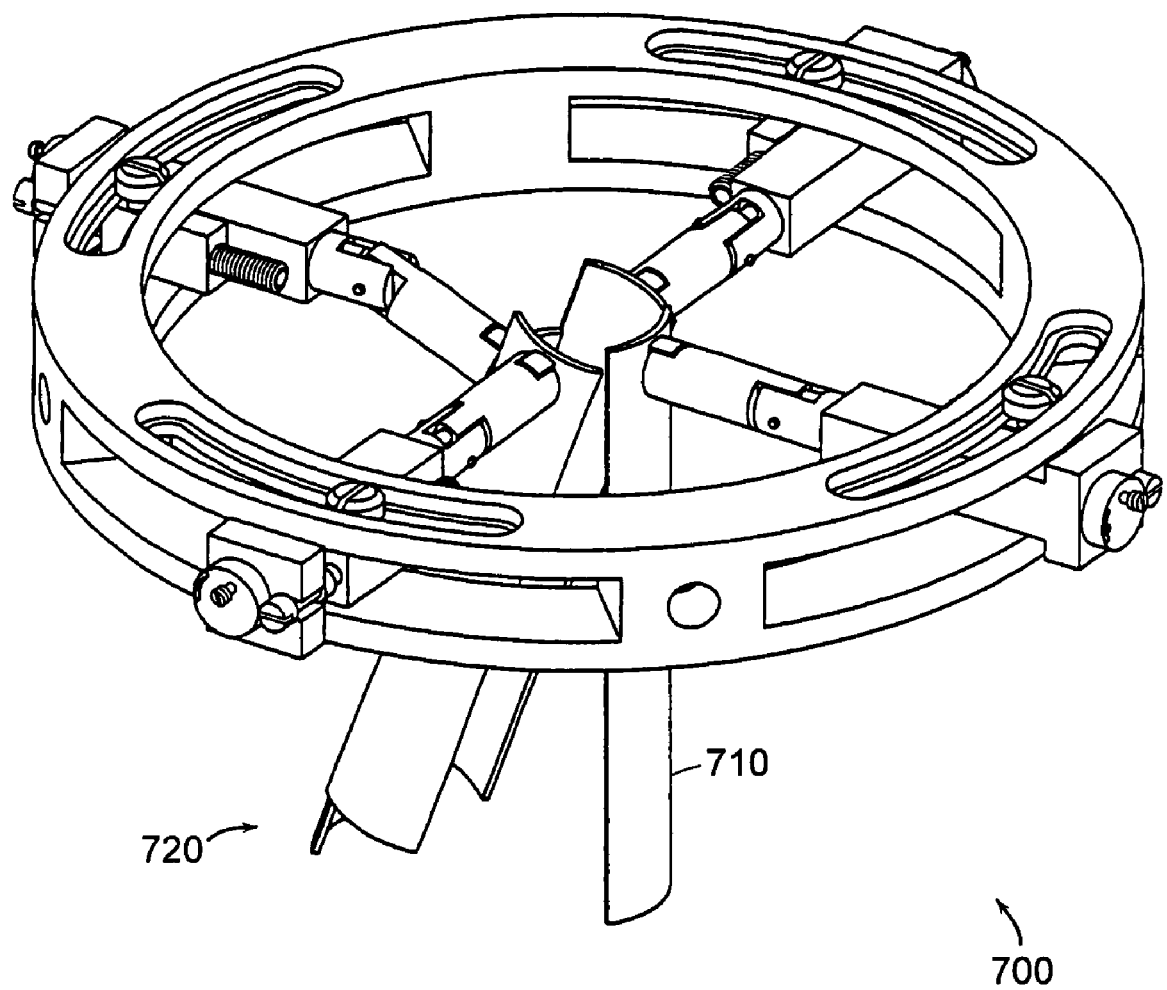
FIG. 7 is a perspective view of a surgical retractor of FIG. 6, but having one retractor blade positioned away from the channel.

FIGS. 5-7 show some exemplary positions of the retractor blades, which are merely shown for the purpose of illustration and should not be considered as limiting to the scope of the invention. The number of combinations of translation(s) and/or rotation(s) of one or more retractor blades provides extensive flexibility to the surgeon or user in exploring the desired operating field with a simultaneous effort to minimize the trauma and size of the incision.

FIG. 5 shows an example 500 where all four retractor blades 510 are positioned in a similar manner with their toes out. FIG. 6 shows an example 600 where all four retractor blades are positioned to establish a channel 610 away from the central axis 620 of frame 630. FIG. 7 shows a similar example 700, as in FIG. 6, with the difference that retractor blade 710 is positioned away from the channel 720.

The retractor system of the present invention can be used in principle for any type of minimally invasive surgical procedure. An example of a surgical procedure is a minimally invasive microscopic thorocotomy without resecting the ribs. The retractor blades can retract the lungs as well as the diaphragm non-traumatically. The retractor can also be used for abdominal procedures, anterior laparoscopy, minimally invasive laparotomy, or retroperitoneal procedures to various surgical tissues within the body. It can also be used for lumbar spinal surgery with either an anterior, posterior, or retroperitoneal approach. The retractor can be placed through the paraspinous muscle using a small sequential dilator without cutting any muscle or underlying fascia. The retractor can be placed over the sequential dilator, which has created a working channel for the retractor. Yet another example of use for the retractor relates to brain surgery and vascular surgery where access space is small or sensitive.

The present invention has now been described in accordance with several exemplary embodiments, which are intended to be illustrative in all aspects, rather than restrictive. The present invention is capable of many variations in detailed implementation, which may be derived from the description contained herein by a person of ordinary skill in the art.

Figure 8:
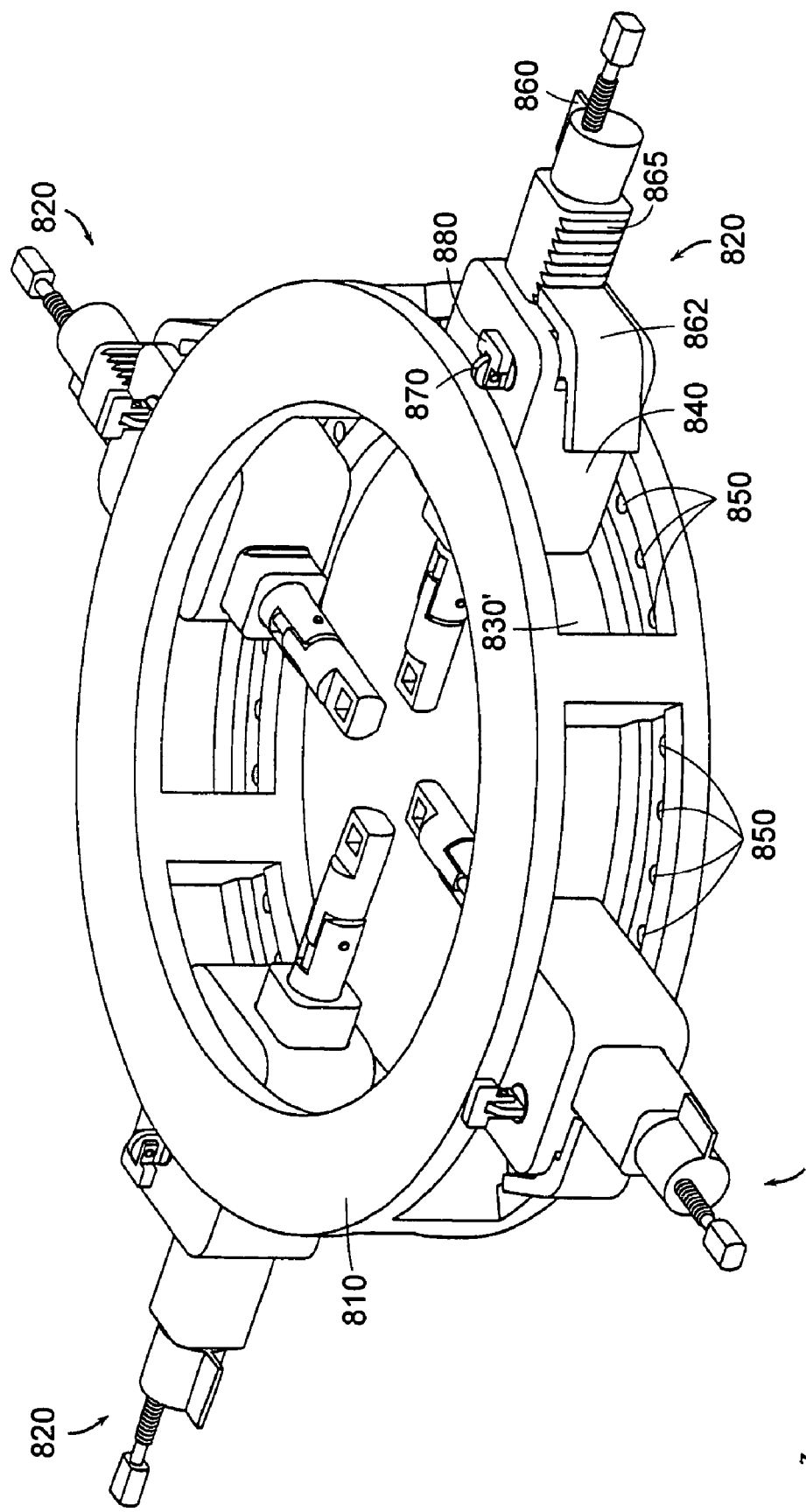
FIG. 8 is a perspective view of another embodiment of a surgical retractor provided in accordance with the present invention.
Figure 9:
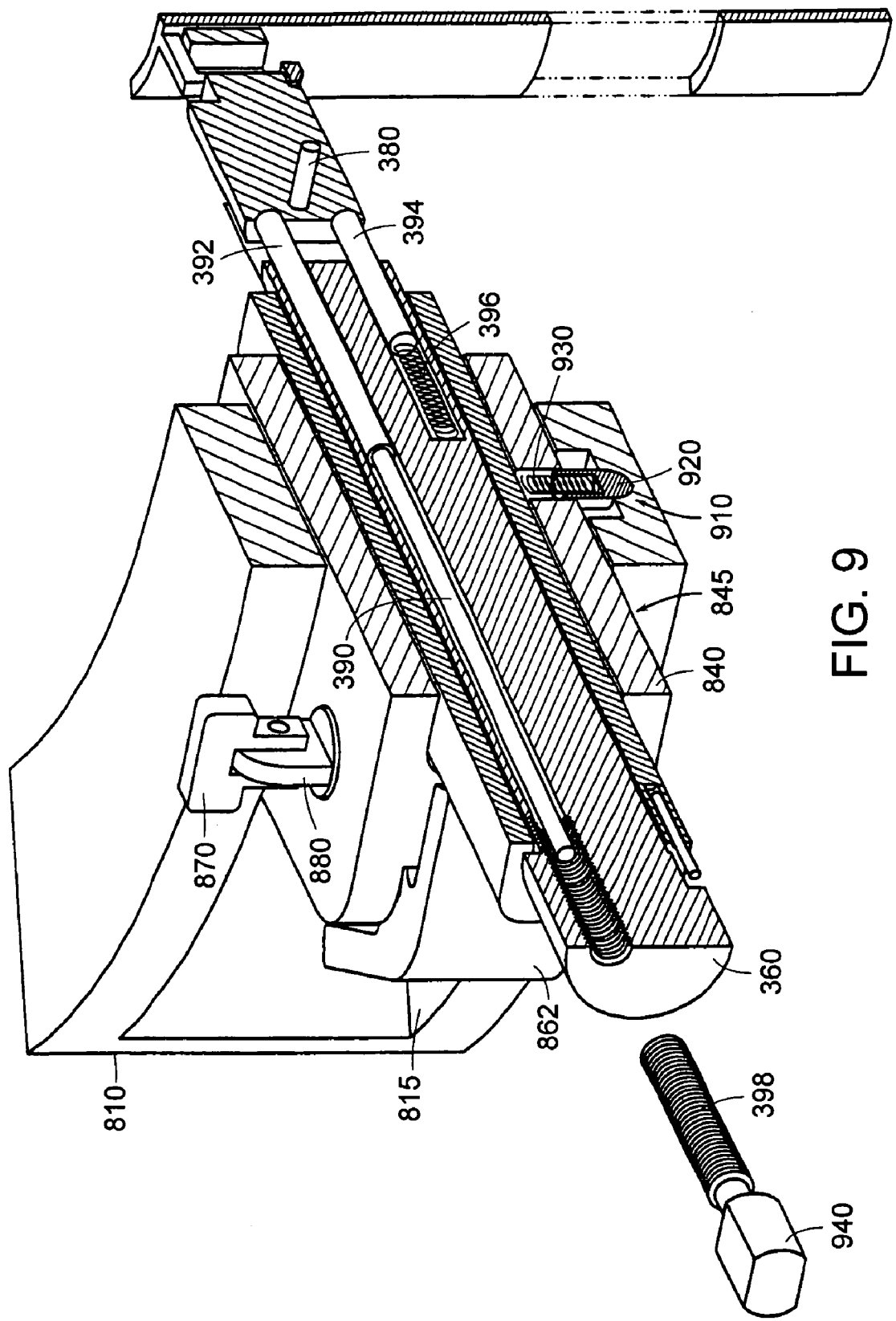
FIG. 9 is a partially cutaway perspective view of another embodiment of positioning means provided in accordance with the present invention.
Figure 10:
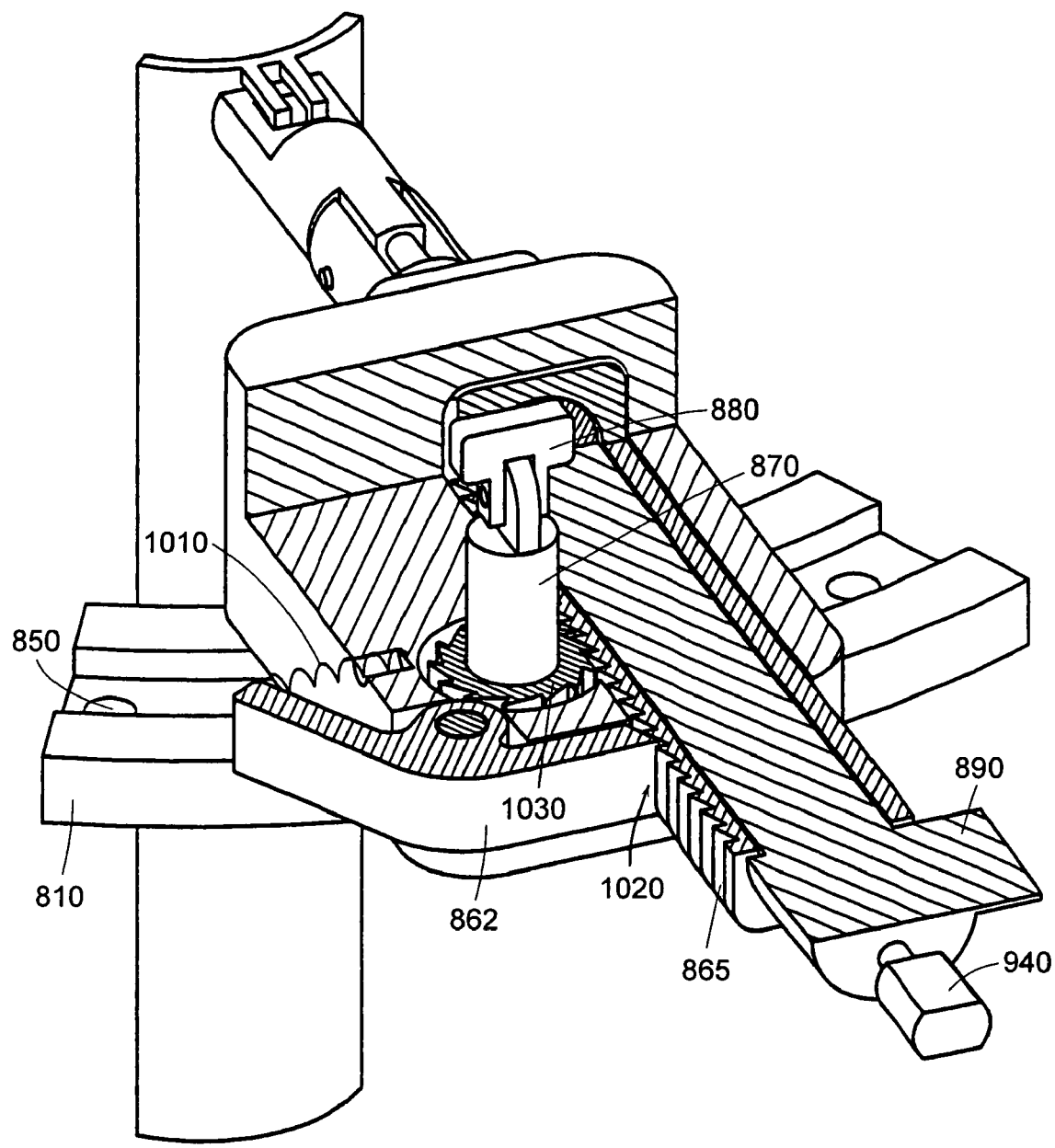
FIG. 10 is a partially cutaway perspective view of a further embodiment of positioning means provided in accordance with the present invention.
Figure 11:
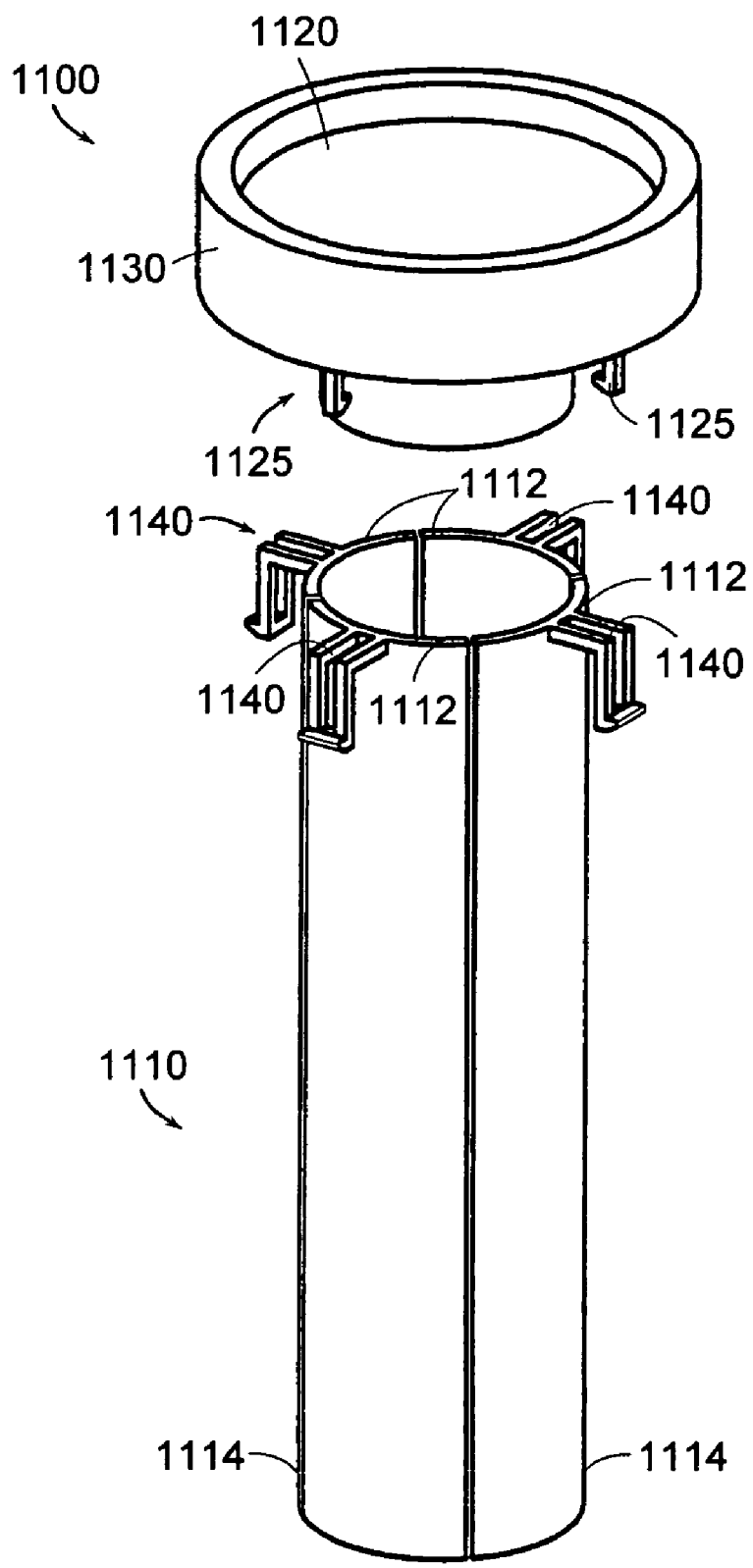
FIG. 11 is a perspective view of a retractor blade assembly positioned above retractor blades provided in accordance with an embodiment of the invention.

FIGS. 8-10 show variations of the frame and positioning means. FIG. 8 shows a variation of frame 810 with positioning means 820 that can be moved inside frame opening 830. Element 840 is capable of moving inside opening 830. X-translation of element 840 is established through a ball-lock mechanism 910 (FIG. 9). The bottom part 815 of frame 810 has openings 850 to allow a ball 920 (or a pin) to slide or lock into. For instance, ball 920 located at the bottom 845 of element 840 can slide into an opening 850 and hold element 840 in that position. Ball 920 can be kept in opening 850 by means of a spring 930. To change position, the user pushes ball 920 out of the opening 850 by, for example, moving element 840. This ball-lock mechanism can be used for a macroscopic X-translation as well as for Y translation and Z-rotation; that is, if multiple balls are placed and located at the bottom 845 of element 840.

Another variation is to have element 860 include a gear system 865 to allow Y-translation. The user can pull out an element 860 from element 840. A lock mechanism 862 can keep element 860 in place when the pulling stops. An extension spring 1010 can be used to ensure that lock mechanism 862 stays in a gear 1020 as shown in FIG. 10. Releasing lock mechanism 862, by pushing in lock mechanism 862, allows element 860 to move back into element 840 to change Y-translation. A rotating element 870 can be used to make microadjustments by rotating element 870 and using a gear system 1030. Rotating element 870 can have an additional element 880 that makes turning of rotating element 870 easier for the user (compare FIGS. 8 and 10). FIG. 9 shows another variation whereby an additional element 890 (part of element 850) can assist the rotation of element 850. Yet another variation is shown in FIG. 9 by additional element 940 that can assist the rotation of element 398. Furthermore, the positioning means can include means to constrain the range of motion in each translation or rotation as is desired for each application of the retractor. For instance, Y-rotation can be constrained by a blocking mechanism (such as a cutout and block that specifies the rotation range) to constrain such a rotation by ±30 degrees, for example, with respect to the coordinate system of the frame.

Yet other variations of the present invention are shown in FIGS. 11-14 including a retractor blade assembly 1100 that can be used to hold the retractors blades 1110 together and position them onto the positioning means. In one embodiment, device or element 1120 is designed to be pushed into element 1130, which can include a collar or rack. If element 1120 is not pushed down, a spring resiliently biases the element 1120 upwards. Element 1120 is connected to one or more attachment means, such as hooks 1125, that are shaped to hook onto a part of the clip or click-on means 1140 of the retractor blades 1110. If the user pushes down element 1120, hooks 1125 are positioned outwards.

Figure 12:
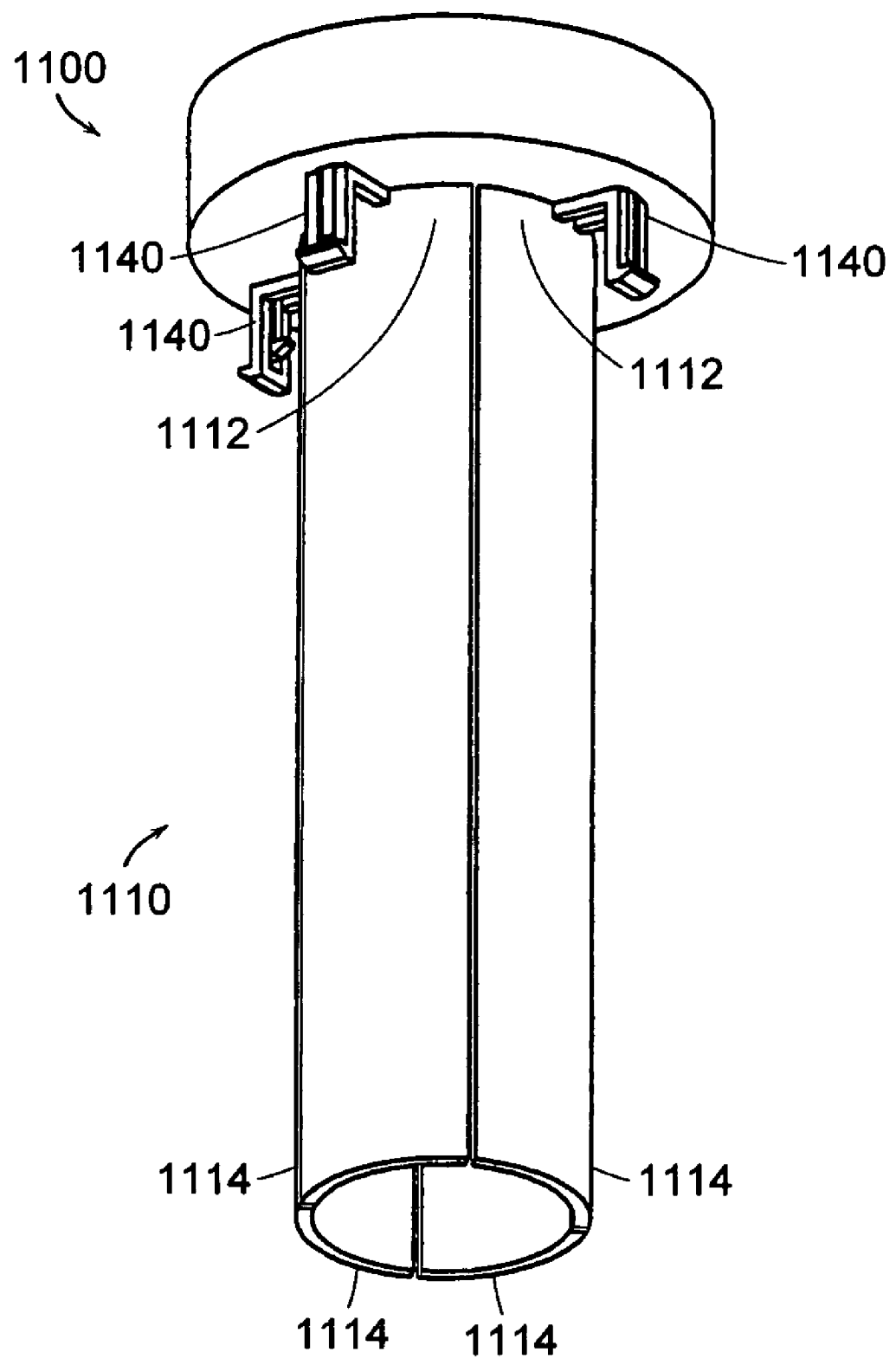
FIG. 12 is a perspective view of the retractor blade assembly positioned on the retractor blades of FIG. 11.
Figure 13:
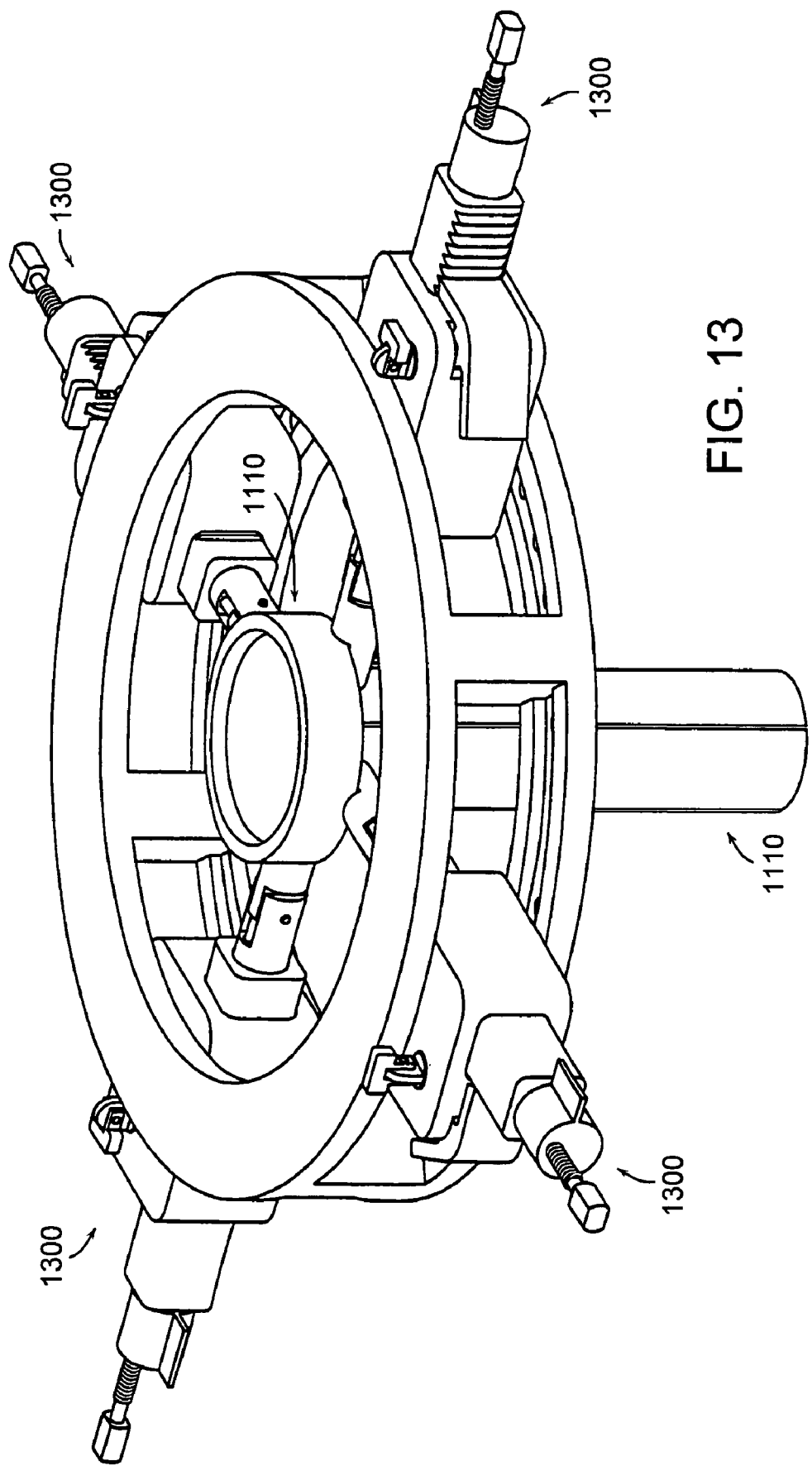
FIG. 13 is a perspective view of the retractor blade assembly of FIG. 11 positioning the retractor blades onto the positioning means shown in FIG. 8.
Figure 14:
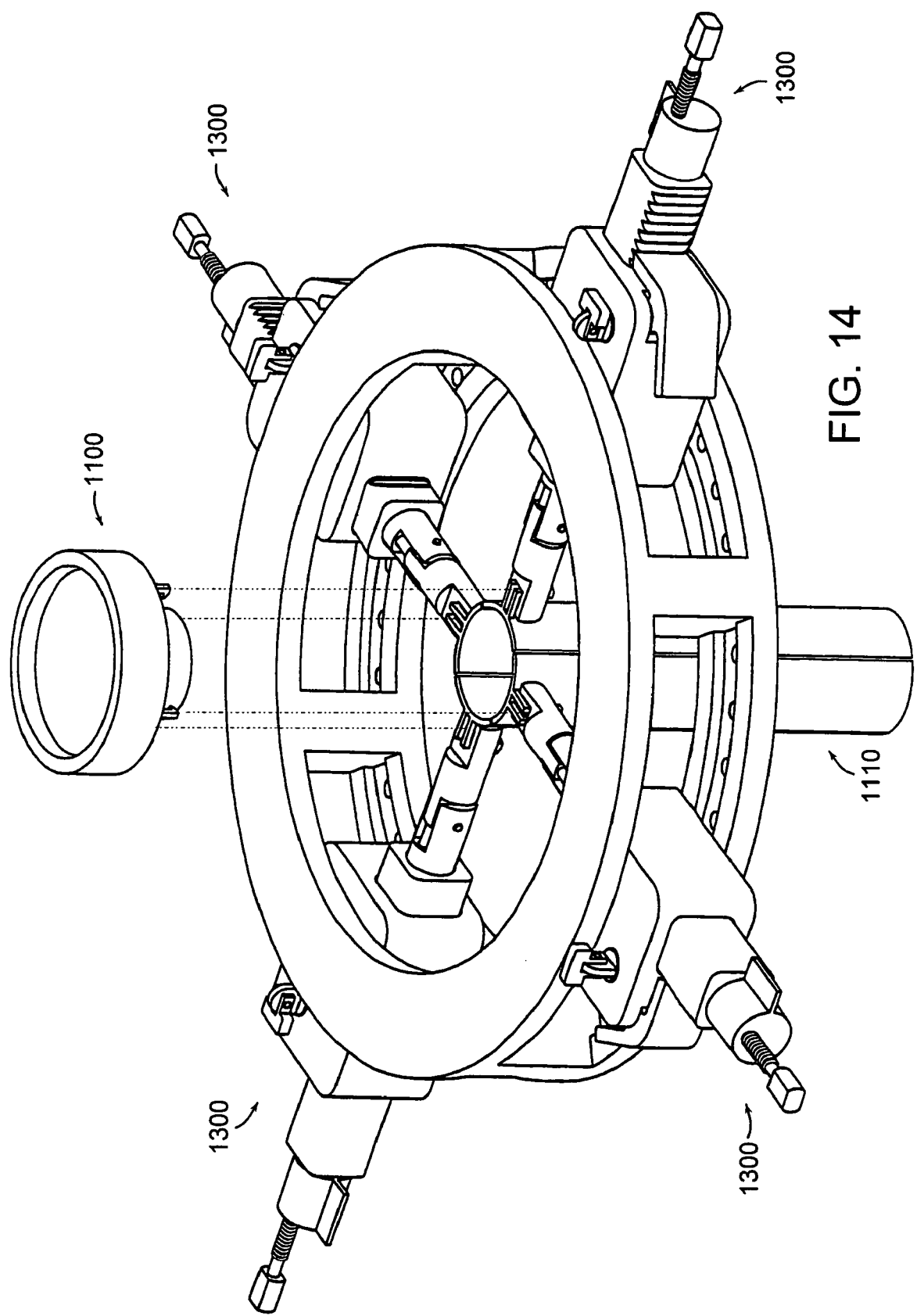
FIG. 14 is a perspective view of the retractor blades attached to the positioning means shown in FIG. 13.

Retractor blade assembly 1100 is then positioned over the retractor blades, which can be aligned such that part of the click-on means 1140 is aligned with hooks 1125. Each retractor blade 1110 includes a proximal end 1112, a distal end 1114, and a major axis extending between the proximal and distal ends. Once aligned, element 1120 is released and the hooks grab onto part of the click-on means 1140. Retractor blade assembly 1100 now holds together and can move all attached retractor blades as shown in FIG. 12. In a particular embodiment, the retractor blades 1110 are substantially parallel to one another when retained by the retractor blade assembly 1100. In other embodiments, the retractor blades 1110 are tapered relative to one another when retained by the retractor blade assembly 1100. The retractor blade assembly 1100 is used to position and attach the retractor blades to the positioning means 1300 as shown in FIG. 13. The attachment of retractor blades is similar as described in FIG. 2. Once the retractor blades are clicked on or attached to positioning means 1300, the user can push down element 1120 to release hooks 1125 from the retractor blades and remove retractor blade assembly 1100 from the retractor blades as shown in FIG. 14.

In other embodiments, a sensor can be placed on the retractor blades, at the inside part, outside part, or within the retractor blade(s). Examples of sensors that are useful are, for instance, pressure sensors to determine the pressure that is established between the retractor blade and the tissue, thermal sensors to determine the temperature in the body near the sensor location on the retractor blade, or a motion sensor that can feed back information regarding the position of the retractor blade as well as position information that can be used to control the retractor blades. In further embodiments, at least one retractor blade can include a position sensor, such as a reflecting, light-emitting, or RF-emitting sensors. Still another variation is the automation of the retractor blade position(s). A control system with gears and motors can be used to automate the positioning instead of manual positioning for both macroscopic and microscopic positioning of the retractor blade(s).

Figures 15, 16:
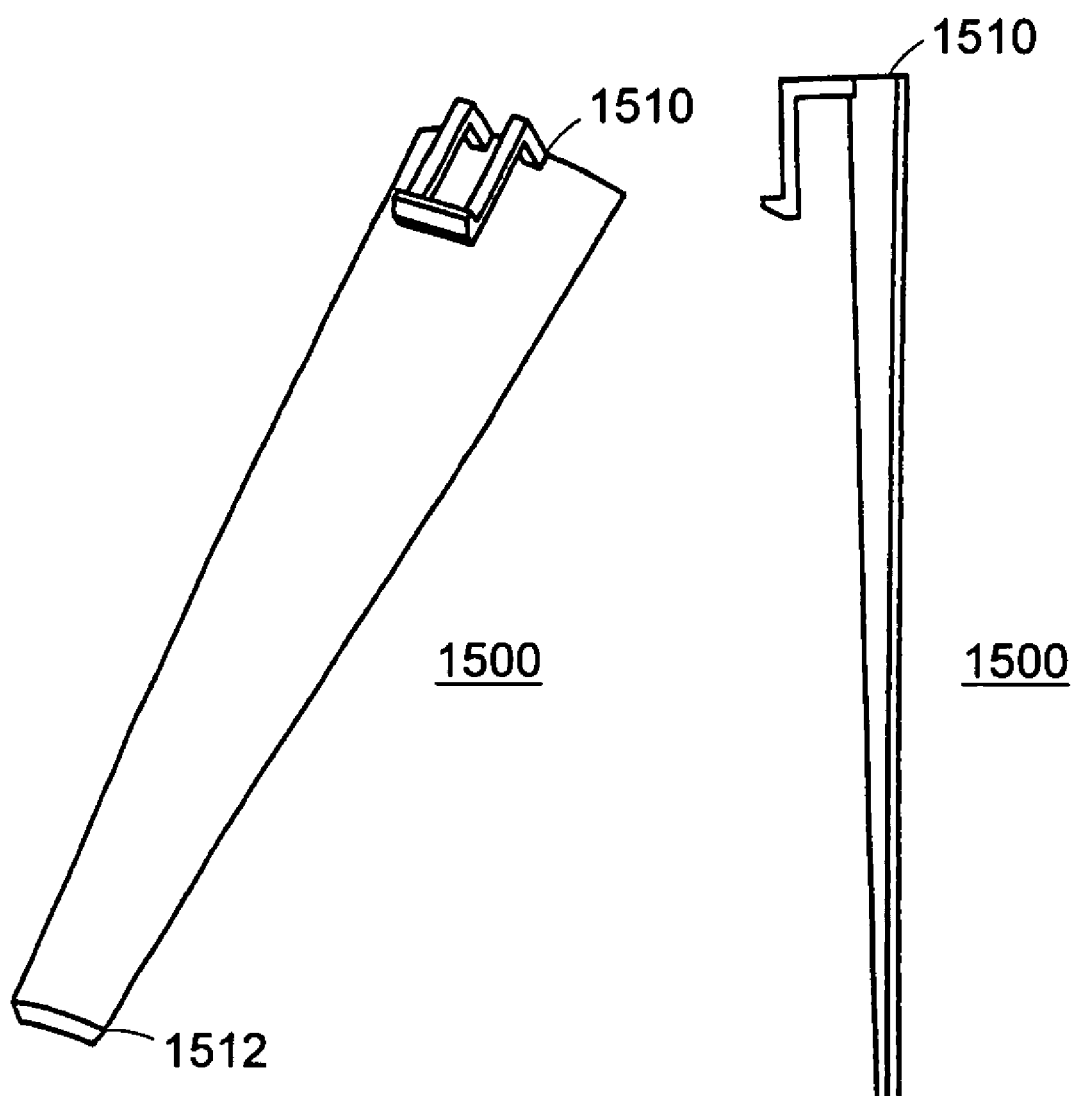
FIG. 15 is a perspective view of another embodiment of a retractor blade provided in accordance with other aspects of the present invention.
FIG. 16 is a side view of the retractor blade illustrated in FIG. 15.

FIGS. 15 and 16 illustrate another embodiment of a retractor blade 1500 that can be used with the surgical retractor provided herein. In this embodiment, the blade 1500 is at least partially tapered from a proximal end 1510 that is attachable to the attachment means 240, for example, to a working or distal end 1512. The blade 1500 can be configured to accommodate specific spinal anatomies. For example, the blade 1500 can be used in interlaminar spinal procedures.

Figure 17:
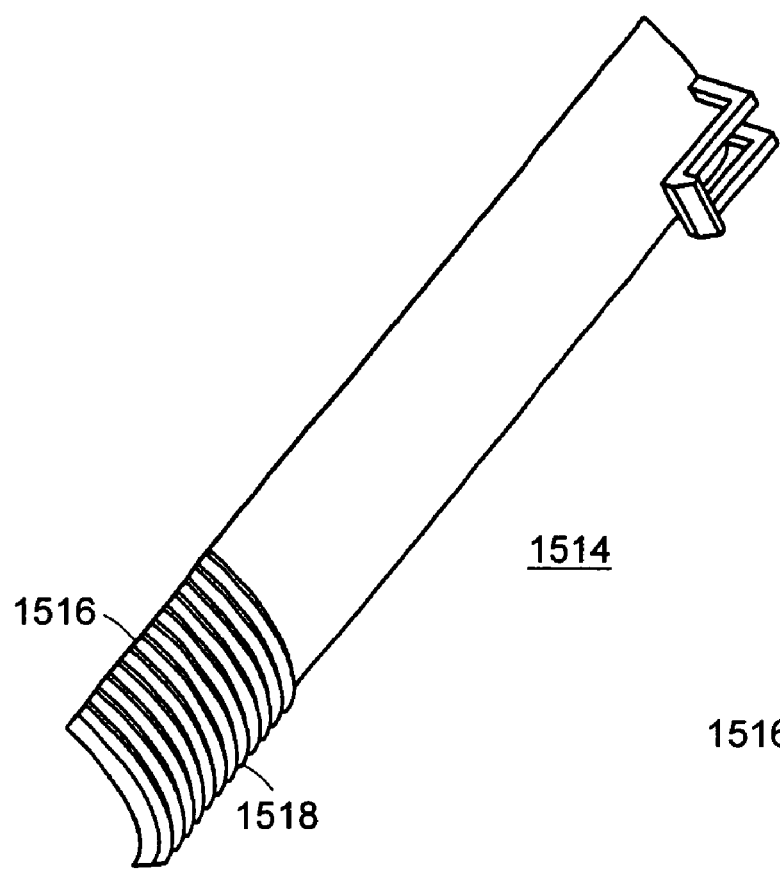
FIG. 17 is a perspective view of a further embodiment of a retractor blade provided in accordance with other aspects of the present invention.
Figure 18:
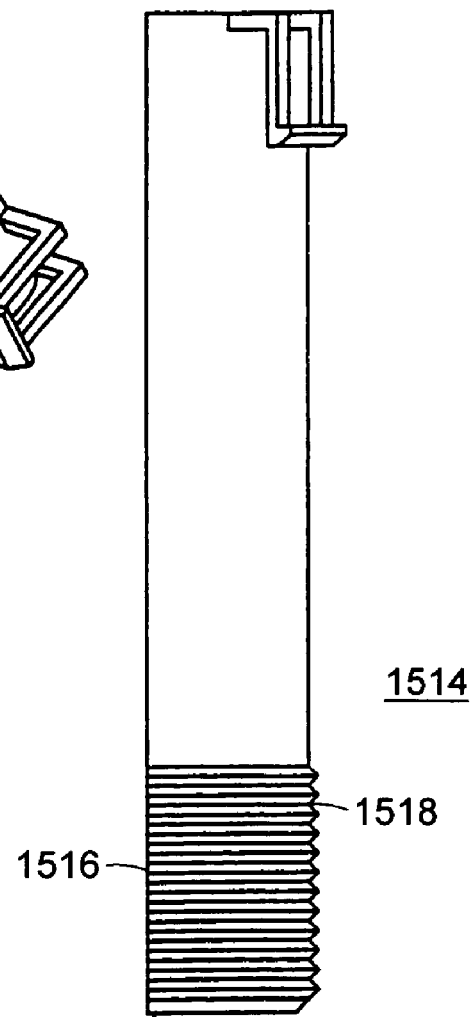
FIG. 18 is a side view of the retractor blade illustrated in FIG. 17.

FIGS. 17 and 18 illustrate another embodiment of a retractor blade 1514 that is configured to prevent or minimize soft tissue slip at a working end 1516 during retraction. The outer surface 1518 can include a textured or other suitable geometry.

What is claimed is:

1. A surgical retractor positioning device, comprising:
   a) a frame;
   b) an arm connected to the frame, the arm including a proximal end, a distal end having a distal end axis, and a major axis, the distal end axis being movable relative to the proximal end, whereby the distal end axis can intersect the major axis at an angle;
   c) at least one blade connected to the distal end of the arm, the blade being fixably rotatable about the major axis; and
   d) a retractor blade assembly that releases the blade from the blade assembly onto the distal end of the arm.

2. The device of claim 1, including at least two arms.

3. The device of claim 2, wherein at least one arm is movable relative to the frame.

4. The device of claim 2, further including a blade connected to the distal end of arm.

5. The device of claim 4, wherein each blade has a proximal end and a distal end, the retractor blades being suspended from the retractor blade assembly at the proximal end of each blade.

6. The device of claim 2, wherein the major axes of the arms are colinear or intersect.

7. The device of claim 6, including at least four arms, each of which having a major axis that is colinear or intersects the major axis of each of the other arms.

8. The device of claim 7 wherein at least one arm is movable along its major axis.

9. The device of claim 8, wherein the major axis of at least one arm can pivot about a point at the frame.

10. The device of claim 9, wherein at least one portion of the frame along which the arm is movable is arcuate.

11. The device of claim 10, wherein the frame is substantially circular.

12. The device of claim 10, wherein the frame is substantially elliptical.

13. The device of claim 1, wherein the blade includes a clip for removably connecting the blade to the arm.

14. The device of claim 1, wherein the blade is at least partially tapered from an end, which is attachable to the arm, to a working end.

15. The device of claim 1, wherein the blade includes an outer surface that is configured to prevent or minimize soft tissue slip during retraction.

16. The device of claim 1, wherein the blade is detachable from the arm.

17. The device of claim 1, further including a sensor at at least one blade.

18. The device of claim 17, wherein the sensor is at least one member selected from the group consisting of a pressure sensor, a thermal sensor, and a motion sensor.

19. The device of claim 1, wherein at least one blade includes a position sensor.

20. The device of claim 19, wherein the position sensor is at least one member selected from the group consisting of a reflective, a light-emitting, and an RF-emitting sensor.

21. The device of claim 1, wherein the arm is controlled by a controller coupled to an actuator.

22. The device of claim 21, further comprising one or more sensors at the arm, blade, or a combination thereof, coupled to the controller, whereby the controller controls the arm based on information provided by the one or more sensors.

23. The surgical retractor positioning device of claim 1, where the retractor blade assembly includes a rack and a hook extending from the rack, whereby the hook releasably attaches to the blade.

24. The retractor blade assembly of claim 23, wherein the retractor blades include at least one clip at the proximal end and, whereby each retractor blade can be affixed to a distal end of an arm of a surgical retractor.

25. The retractor blade assembly of claim 24, wherein each hook at the rack is slidably engageable with the at least one clip of the retractor blade while the blades are suspended within the rack.

26. A surgical retractor positioning device, comprising:
   a) a circular frame;
   b) a plurality of arms connected to the frame, each arm including a proximal end, a distal end having a distal end axis being movable relative to the proximal end, and a major axis that extends between the proximal and distal ends, whereby the distal end axis can intersect the major axis at an angle, the major axis of at least one arm being able to pivot about a point at the frame; and
   c) a retractor blade connected to the distal end of each arm, each blade being fixably rotatable about the major axis.

27. The device of claim 26, wherein each blade includes a clip for removably connecting the blade to an arm.

28. The device of claim 26, further including a retractor blade assembly for attaching the blades to the distal end of each arm.

29. A method of forming a surgical working field in a patient, comprising the steps of:
   making an incision in a patient;
   releasing a plurality of blades from a retractor blade assembly onto distal ends of arms of a surgical retractor, each arm of the surgical retractor including a major axis, a proximal end, and a distal end having a distal end axis, the distal end axis being movable relative to the proximal end, whereby the distal end axis can intersect the major axis at an angle, the blades being adjustable from a collapsed, reduced diameter configuration to an extended, increased diameter configuration;
   positioning the surgical retractor over the incision;
   introducing the blades in the collapsed configuration into the incision in the patient;
   expanding the blades within the incision to the increased configuration to create the working field in the patient; and
   rotating at least one blade relative to a major axis of an arm and affixing the blade in a desired position.

30. The method of claim 29, wherein the steps of moving the at least one retractor blade is carried out under automated control.

* * * * *